(12) United States Patent
Al Fadhel

(10) Patent No.: US 11,499,904 B2
(45) Date of Patent: Nov. 15, 2022

(54) IN VITRO DISSOLUTION TEST METHOD FOR FLUTICASONE PROPIONATE AND OTHER INHALED DRUGS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Salman Al Fadhel, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 457 days.

(21) Appl. No.: 16/788,748

(22) Filed: Feb. 12, 2020

(65) Prior Publication Data
US 2021/0247287 A1 Aug. 12, 2021

(51) Int. Cl.
*G01N 15/02* (2006.01)
*A61K 9/00* (2006.01)
(Continued)

(52) U.S. Cl.
CPC ....... *G01N 15/0255* (2013.01); *A61K 9/0043* (2013.01); *A61K 9/0073* (2013.01);
(Continued)

(58) Field of Classification Search
CPC ....... G01N 1/2208; G01N 2035/00198; G01N 2013/006; G01N 2015/0261;
(Continued)

(56) References Cited

U.S. PATENT DOCUMENTS 3,791,222 A * 2/1974 Goodhart ................ B01F 35/20
73/866
3,802,272 A * 4/1974 Bischoff ................ G01N 13/00
73/866
(Continued)

FOREIGN PATENT DOCUMENTS

WO    WO 00/46597    *   8/2000
WO    WO 2021/093975 A1 *  5/2021

OTHER PUBLICATIONS

Son, et al. ; Optimization of an In Vitro Dissolution Test Method for Inhalation Formulations ; Dissolution Technologies ; May 2010 ; 9 Pages.

*Primary Examiner* — Hoa Q Pham
(74) *Attorney, Agent, or Firm* — Oblon, McClelland, Maier & Neustadt, L.L.P.

(57) ABSTRACT

An apparatus and method for testing dissolution properties of a drug, especially anti-inflammatory drugs administered by aerosol into the respiratory system. The apparatus shortens the time it takes for a drug to dissolve and thus provides for rapid testing of new drugs for quality control as well as for regulatory purposes. It is suitable for evaluating bioequivalence or to study the pharmacokinetics of drugs administered into the respiratory system. This method shortens dissolution times for testing a drug to about 10 and 20 minutes and thus provides for rapid testing.

20 Claims, 11 Drawing Sheets

(51) Int. Cl.
*G09B 23/30* (2006.01)
*G01N 15/00* (2006.01)
(52) U.S. Cl.
CPC .... *G09B 23/303* (2013.01); *G01N 2015/0011* (2013.01); *G01N 2015/0261* (2013.01)
(58) Field of Classification Search
CPC .... A61K 9/0075; A61K 9/145; A61K 9/0073; A61K 2300/00; A61K 31/137; A61K 31/46; A01N 25/12; A61J 3/02
USPC ........ 356/246, 440; 73/23.23, 61.71, 846.91, 73/866; 366/208, 140, 142, 213; 422/270, 277
See application file for complete search history.

(56) References Cited

U.S. PATENT DOCUMENTS

| | | | | |
|---|---|---|---|---|
| 5,816,701 | A * | 10/1998 | Martin | G01N 13/00 366/208 |
| 8,584,539 | B2 * | 11/2013 | Wright | G01N 33/15 73/866 |
| 10,022,303 | B2 * | 7/2018 | Bosch | A61K 31/137 |
| 2005/0238540 | A1 * | 10/2005 | Swon | B01F 31/441 422/561 |
| 2012/0135046 | A1 | 5/2012 | Wu et al. | |
| 2014/0161895 | A1 | 6/2014 | Miller et al. | |
| 2015/0224062 | A1 | 8/2015 | Williams, III et al. | |
| 2018/0318170 | A1 | 11/2018 | Bosch et al. | |

\* cited by examiner

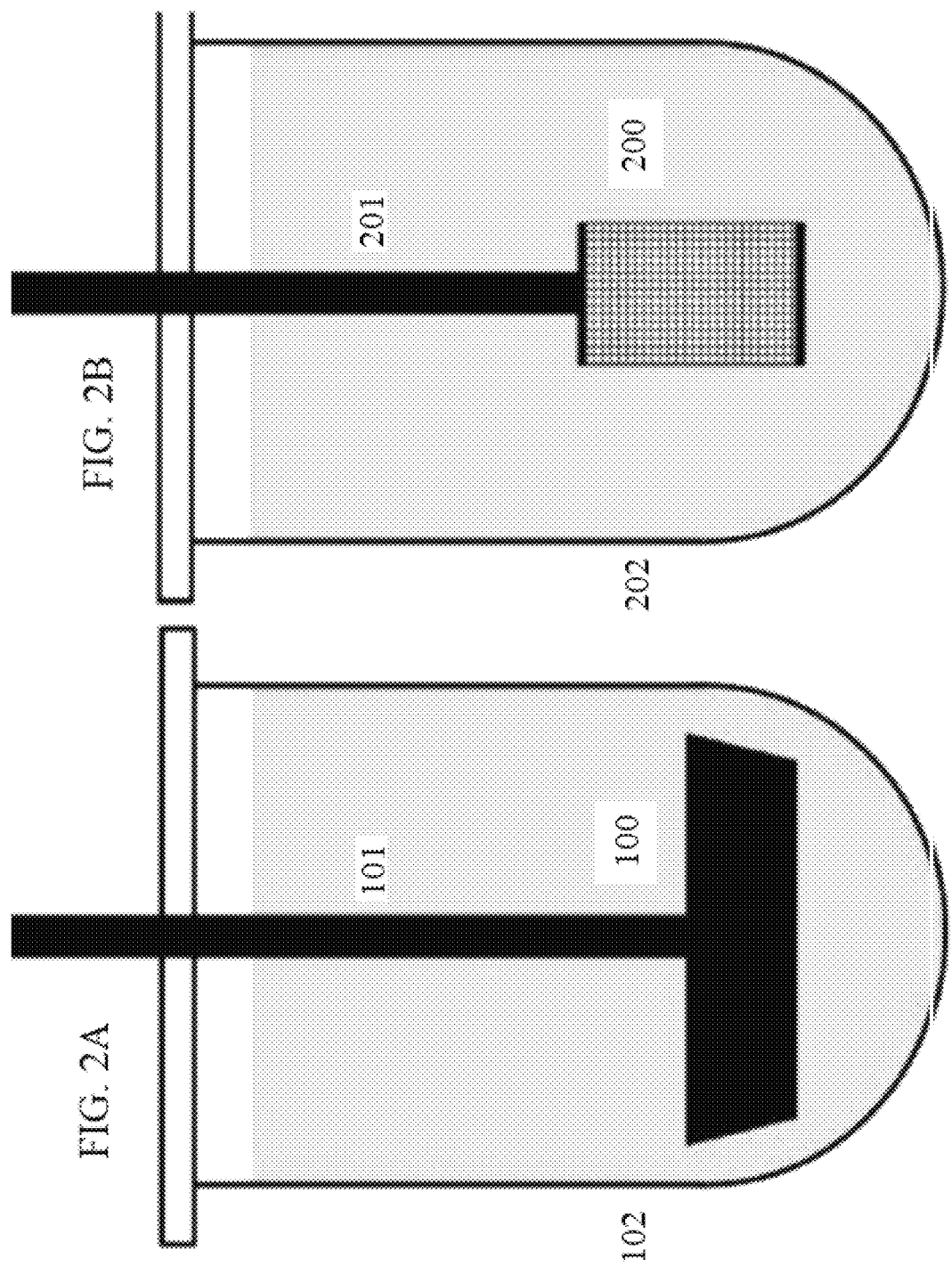

IN VITRO DISSOLUTION TEST METHOD FOR FLUTICASONE PROPIONATE AND OTHER INHALED DRUGS

BACKGROUND OF THE INVENTION

Field of the Invention

The invention pertains to the fields of pharmacology, respiratory medicine, and medical devices.

Description of the Related Art

The essential function of the respiratory tract is to transfer oxygen from inspired air to the blood and release carbon dioxide into expired air. The airway to the human lung divides for 23 generations until it reaches the alveolar sac; Patton J S. (1996). *Mechanisms of macromolecule absorption by the lung*, Advanced Drug Delivery Reviews; 19: 3-36. The upper lung airway leads into the body from the thick-walled trachea in the upper respiratory tract and progressively thins as it branches down the airway tree to the alveoli of the lung which has very thin walls and a large surface area where oxygen is absorbed and carbon dioxide released; see FIG. 1A which describes various segments or branches of the respiratory system and their physical parameters.

Drugs are administered into the respiratory system by various modes. FIG. 1B depicts administration of a metered dose of an inhaled drug as well as the fate of the drug depending on whether the drug is deposited in the lungs or elsewhere in the respiratory system and swallowed. In order to deposit in the lung, an inhaled aerosolized drug must travel through the upper respiratory tract including the oral and nasal cavities, the pharynx, and the larynx, and through the lower respiratory tract including the trachea and extending all the way to the terminal bronchiole alveoli in the lungs. A drug deposited in the lungs will be absorbed into the systemic circulation and thus has the potential to exert a local and systemic therapeutic effect. However, some of the dose of an inhaled drug will be removed by mucociliary clearance. This is a natural self-clearing mechanism of the respiratory system airways that removes inhaled particles such as smoke or dust before they can reach the delicate tissue of the lungs.

Depending on how a drug is absorbed, it may be removed from the body unchanged in the urine or by the metabolism in the liver, followed by excretion of the metabolite in the urine or bile; Hochhaus G: *New developments in corticosteroids*. Proc Am Thorac Soc 2004; 1(3):269-274. Unlike a drug absorbed through the lungs, a swallowed drug is subject to the first pass effect, a phenomenon of drug metabolism whereby the concentration of a drug is greatly reduced in the liver before it reaches the systemic circulation.

The deposition (impaction) of drug particles within the respiratory system depends on the size of the particles. Particles that are too large impact in the upper respiratory system are subject to mucociliary clearance and are swallowed. Particles that are too small are inhaled, can reach the lungs, but fail to impact and are exhaled. FIG. 1C generally depicts the effects of particle size on deposition or impaction in the respiratory system. Particles with an aerodynamic diameter within a size range of <5 µm are most likely to deposit in the lungs. Particles greater than 5 µm in diameter are most likely to be deposited in the upper airways including the mouth, nose and pharynx where most are eventually swallowed and thus do not impact and deliver drug locally to the lungs. For many drugs, deposition onto the conducting airways comes from drug particles within the range of 2 and 5 µm which will deposit in the conducting airways by impaction and sedimentation. Smaller drug particle sizes of many drugs in the range of 0.5-2 µm in diameter, mostly deposit in the alveoli by Brownian motion with some gravitational sedimentation; Newman S et al. (1983), *Therapeutic aerosols 1—physical and practical considerations*. Thorax 38(12): 881-886.

There is a need for a convenient drug dissolution test which can accurately and easily determine the dissolution properties and pharmacokinetic properties of a drug, compare dissolution properties of different batches or sources of the same drug, evaluate bioequivalence of an approved drug and a generic version of the drug, or discover desirable drug formulations for targeting the lung or other parts of the respiratory system. Such a test should be standardizable and useful for quality control and/or determining whether a drug meets regulatory requirements. While various systems are known, no dissolution method has been universally accepted; Arora D, Shah K A, Halquist M S, Sakagami M: *In vitro aqueous fluid-capacity-limited dissolution testing of respirable aerosol drug particles generated from inhaler products*. Pharm Res 2010; 27(5):786-795; Davies N M, Feddah M R: *A novel method for assessing dissolution of aerosol inhaler products*. Int J Pharm 2003; 255(1-2):175-187. Son, et al. used a paddle apparatus with membrane holder, flow through cell or Franz diffusion cell. However, the dissolution test results for certain drugs such as budesonide (an important inhaled corticosteroid (ICS)) were found to differ depending the selection of a dissolution medium. Thus, for determination of dissolution properties of a particular drug preparation an adapted dissolution medium for that preparation is used. This complicates making a controlled comparison of the dissolution properties for different drugs, generic and approved forms of the same, drug or different preparations of the same drug having different excipients; Arora et al; Davies et al.; Pham S, Wiedmann T S: *Note: dissolution of aerosol particles of budesonide in Survanta, a model lung surfactant*. J Pharm Sci 2001; 90(1):98-104; and Son Y J, Horng M, Copley M, McConville J T: *Optimization of an in vitro dissolution test method for inhalation formulations*. Dissolution Technologies 2010; 6-13; Stoloff S W, et al., *Updates on the use of inhaled corticosteroids in asthma*. Curr Opin Allergy Clin Immunol 2011; 11(4):337-344.

Prior devices like those described by Son, et al. position a collection cup or collection disc at the bottom of a dissolution vessel and circulate the dissolution medium with a paddle inserted into the top of the vessel. However, this configuration only results in a slow rate of release of the drug in the collection cup. In contrast, the invention provides for a superior rate of drug dissolution by inserting the collection cup into a rotating basket. This increases the rate of release (dissolution) of the drug impacted on the collection cup. Preferably, the insert is positioned in the basket with the side having impacted drug faced down.

Inhaled corticosteroids (ICS) constitute an important class of anti-inflammatory respiratory drugs and are used for treatment of inflammatory respiratory diseases such as chronic obstructive pulmonary disease (COPD) and asthma; Reddel H K, et al., *Year-in-review 2010: asthma, COPD, cystic fibrosis and airway biology*. Respirology 2011; 16(3): 540-552; and Rossi G A, et al., *Safety of inhaled corticosteroids: room for improvement*. Pulm Pharmacol Ther 2007; 20(1):23-35. However, currently, it is difficult to provide controlled comparisons of different preparations of ICSs because of the variety of different devices, formulations and dosages in use as well as both originally approved and generic versions of these drugs.

With these problems and drawbacks with current devices and dissolution tests in mind, the inventors sought to develop a modified dissolution test apparatus and method that provides rapid, accurate and comparable dissolution test results.

SUMMARY OF THE INVENTION

Among its various aspects, the invention is directed to a method for testing drugs for their ability to dissolve in the respiratory system. This method facilitates determination of dissolution properties of inhaled drugs, especially the dissolution properties of the fraction of the drug impacting the lungs or other select segments of the respiratory tree. The apparatus and methods disclosed herein provide for rapid dissolution testing of new inhalable drugs as well as comparisons of different batches or preparations of a drug (such as comparison of a generic drug to an originally approved drug) for example, to meet regulatory criteria, for quality control, bioequivalence or to study the pharmacokinetics of drugs administered into the respiratory system. This method shortens dissolution times for testing a drug to about 10 and 20 minutes and thus provides for rapid testing. Another aspect of the invention is a modified dissolution apparatus for performing the dissolution test. The apparatus hosts new elements such as an impaction insert for a next generation impactor and redesigned basket for a dissolution device which provides a simple and cost effective version of dissolution test proposal for inhaled drugs.

Nonlimited embodiments of the invention include the following.

A cylindrical basket having round bottom base, a top base, and a cylindrical open mesh shell; wherein the inside of the basket is configured to hold an impaction insert from a modified collection cup from a particle impaction device; and wherein the top is configured to connect to a rotatable shaft. This basket is sized and configured to accommodate an impaction insert from a drug particle impactor such as a next generation impactor (NGI). An impactor can be attached to a source of an inhalable medicine or drug such as a metered-dose inhaler (MDI), dry powder inhaler, nebulizer or soft mist inhaler.

This cylindrical basket typically has a bottom base and/or top base and is configured to hold an impaction insert from a next generation impactor (NGI) in contact with a dissolution buffer in a vessel into which the basket can be immersed. The inside diameter of the cylindrical basket may the same as the outside diameter of the impaction insert so the insert can be snugly fit into the basket. In other embodiments, the basket will have a slit through which the impaction insert may be slid into the basket or have a clip or other mechanical fitting to receive and secure the impaction insert inside the basket. In other embodiments, the impaction insert may be placed into the basket via the top base or the bottom base, either of which can be irreplaceably removable from the cylinder, for example, by a top of bottom fitting with threads into which the top or bottom base can be screwed to attach it to the rest of the basket. In a preferred embodiment, the drug collected on the top of the impaction insert is covered and sealed with a membrane. The membrane-sealed insert is then transferred and loosely fit into the rotating basket thus enhancing release of the drug during rotation of the basket. Typically the membrane covered side having impacted drug of the insert is positioned faced down in the basket. Though in other embodiments, it may be positioned face up or vertically along the axis of rotation for the basket, like a coin standing on end.

During its use in a dissolution test, the basket will contain an impaction insert from a drug particle impactor, sifter, or sizer, such as a next generation impactor. Typically, a top of an insert or disc containing impacted drug will be covered by a membrane prior to its insertion into the basket of the dissolution device disclosed herein. In preferred embodiments, the insert or disc is loosely fit into the basket to permit it to move during rotation of the basket. In other embodiments, the insert or disc may be securely fixed in the basket.

In some embodiments the bottom base and top base of the basket are about 90, 90.2, 91, 92, 93, 94, 95, 96, 97, 98, 99, 100, 101, 102, 103, 104, 105, 106, 107, 108, 109, 110, 110.2, 111, 112, 113, 114, or 115 in diameter. The height of the cylindrical basket may range from 30, 31, 32, 33, 34, 35, 36, 37, 38, 39, 40, 41, 42, 43, 44, or 45 mm. Though the actual basket size (diameter and height) may be large or small enough to efficient fit an impaction insert and keep it in contact with a dissolution medium in a vessel into which the basket is immersed.

The cylindrical basket may further comprise a clip or other mechanical fitting for attaching the top of the basket to a rotating shaft. Such a fitting and/or top base may comprise a retention spring and a vent hole. The shaft preferably rotates at a speed of 50, 60, 70, 80, 90, 100, 110, 120, 130, 140 or 150 rpm.

The cylindrical basket may be made of any suitable material durable once immersed in a dissolution buffer and which permits contact between the contents of the basket, such as an impaction insert sealed with an artificial lung membrane. Typically the mesh comprises a stainless steel, aluminum or other metal mesh, though durable plastics, ceramics and other suitable materials can be used in some embodiments. In some embodiments this mesh ranges from #20 to #40 mesh. Mesh openings may range from 0.1, 0.2, 0.3, 0.4, 0.5, 0.6, 0.7, 0.8, 0.9 mm to 1.0 mm in diameter.

Another embodiment of the invention is a drug dissolution measurement system comprising a next generation impactor (NGI) comprising a collection cup having an impaction insert, a lung simulation membrane, the cylindrical basket, in one or more of its embodiments, attached to a rotatable shaft, and a vessel containing an aqueous medium. Thus system may further comprise drug impacted on the impaction insert, such as an impacted inhalable anti-inflammatory drug impacted on the impaction insert. In this system, the lung simulation membrane is a polycarbonate membrane or a polyvinylidene difluoride (PVDF) membrane. Other types of membranes suitable for use with the device disclosed herein may be selected by those skilled in the art.

This system may further comprise a rotary mixture attached to the rotatable shaft and/or a chromatography system suitable for determining the concentration of a drug in the aqueous medium.

Another embodiment of the invention is directed to a method for determining dissolution properties of an aerosolized drug comprising applying the drug to a next generation impactor (NGI) under conditions suitable for impacting particles of the drug in the collection plates of the NGI, recovering impacted drug particles on one or more impaction inserts from the collection plates, sealing the one or more collection plates in a lung simulation membrane, inserting the collection plate sealed within the lung simulation membrane into the basket as disclosed herein, submerging the basket containing the membrane covered impaction inserts in a dissolution medium contained in a vessel, and detecting an amount of the drug which dissolves into the medium.

In some embodiments of this method the dissolution medium is water, phosphate buffered saline, or a simulated lung fluid. In other embodiments, the impaction insert contains drug particles ranging in size from 3.3 to 4.7, 1.1 to 3.3, or 0.45 to 1.1 μm in diameter.

In some embodiments, the impacted drug is the substantially pure drug without admixture with another drug and without excipients, surfactants, preservatives, or carriers. In other embodiments, the impacted drug particles comprise the drug along with excipients, surfactants, preservatives or carriers. In some embodiments, impacted drug particles will contain a mixture of 2, 3 or more drugs.

In other embodiments of this method, the impaction insert sealed with a polycarbonate or polyvinylidene difluoride (PVDF) membrane.

In preferred embodiments of this method amount of drug or other tested compound or material dissolved into the dissolution medium is detected after a period of no more than 5, 10, 15, 20, 25 or 30 minutes, most preferably no more than 10 minutes.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A depicts the paddle 100, rotatable shaft 101, and vessel 102 of a USP type 1 (paddle) drug dissolution system. USP pharmacopeia (2005) Chapter <601>.

FIG. 2B depicts the basket 200, rotatable shaft 201, and vessel 202 of a USP type 2 (basket) drug dissolution system. Typically, the basket element of the device is larger than the basket element specified by the pharmacopeia or by Marple, et al., J Aerosol Med. 2003 Fall; 16(3):283-99. Advantageously, the size of the basket may be customized to accommodate the impaction insert. (USP pharmacopeia (2005) Chapter <601>); Marple, et al., J Aerosol Med. 2003 Fall; 16(3):283-99.

FIG. 3A describes the disassembled parts of the collection cup of the NGI. Insert or disc (25) fits at cup (15). Drug collected on top of the insert or disc is covered by a membrane and then secured with ring (30) prior to transfer to a dissolution vessel. (Marple, et al., J Aerosol Med. 2003 Fall; 16(3):283-99); (adapted from Copley, 2003) "Quality solution for inhaler testing". Nottingham, UK.

DETAILED DESCRIPTION OF THE INVENTION

Figure 1A:
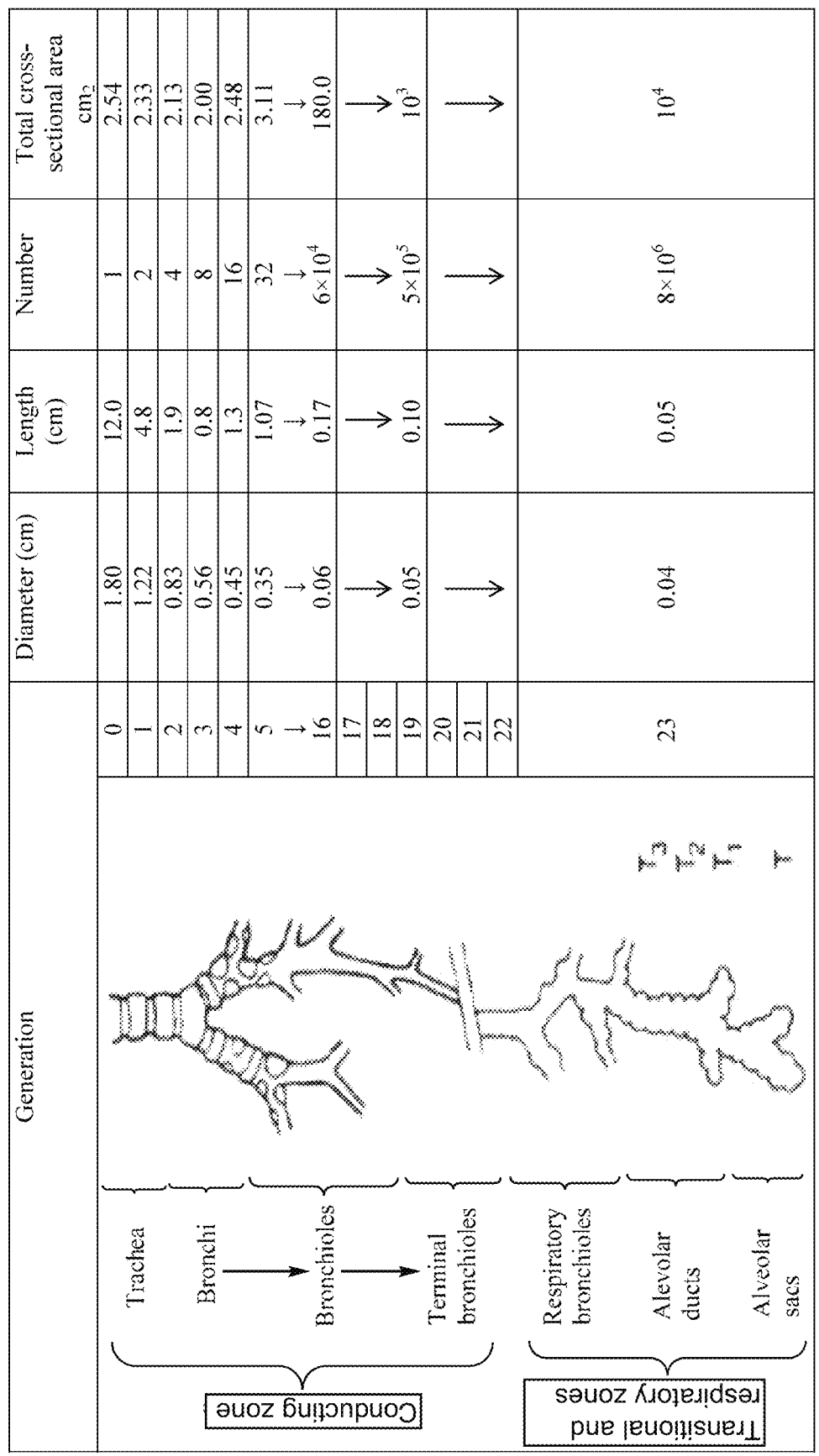
FIG. 1A depicts the various branches of the respiratory system and their physical dimensions. Adapted from Patton, 1996, *Mechanisms of macromolecule absorption by the lung*, Advanced Drug Delivery Reviews; 19: 3-36.
Figure 1B:
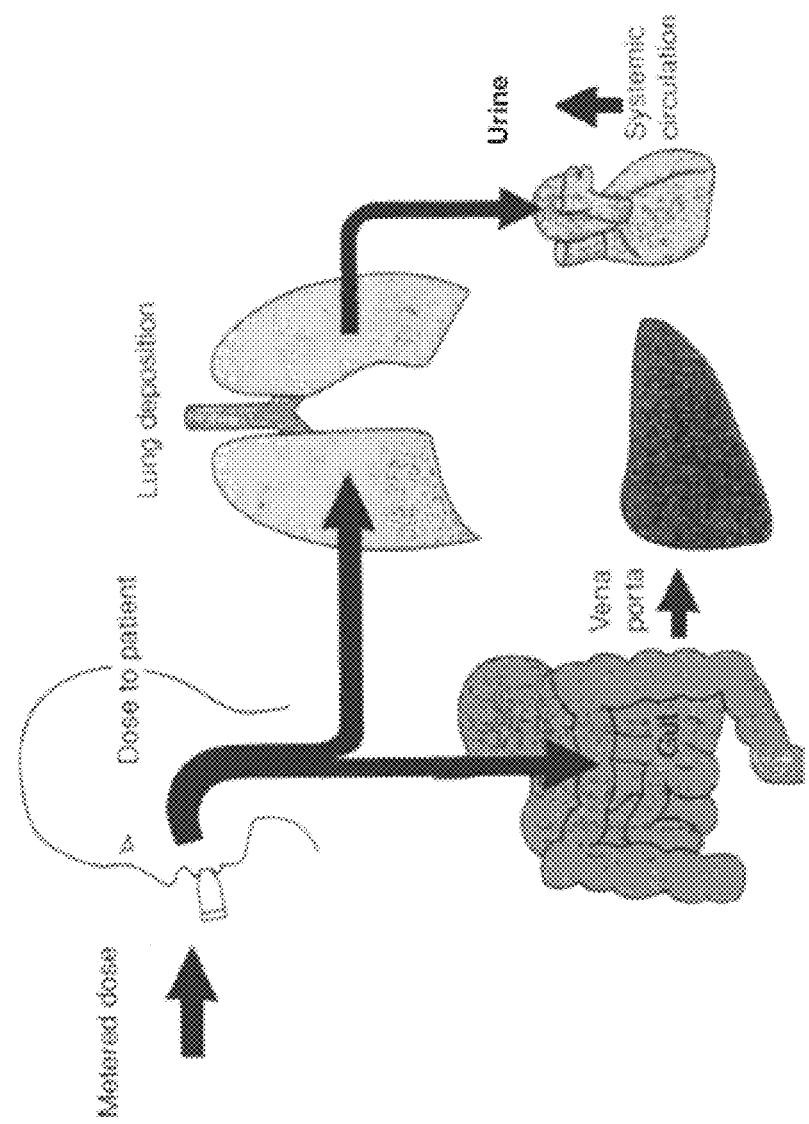
FIG. 1B provides a general overview of the fate of inhaled corticosteroid (ICS) drug deposition. Adapted from Bisgaard et al, 2002, *Drug delivery to the lung*, Marcel Dekker, 162.

The invention provides a rapid, convenient and simple way to determine the dissolution properties of an inhaled drug, such as an anti-inflammatory drug administered in an aerosol form to a patient. Determination of these properties is useful for quality control during production of a drug, assessment of bioequivalence of a generic drug, as well as to comply with regulation. The invention provides a superior dissolution test by use of a modified dissolution basket adapted to easily measure the dissolution properties of drug particle fractions from a modified next generation impactor. Advantageously, a method using the apparatus of the invention can determine dissolution properties of an inhaled drug within 5, 10 to 20 minutes. The method is typically used to determine the quality of an inhaled drug preparation, such as relative distribution of particle sizes and delivered dose uniformity, and thus is a good candidate for use in showing that a drug preparation complies with worldwide regulation.

Respiratory diseases for which inhalable or aerosolized drugs may be tested using the apparatus and methods described herein include, but are not limited to, pneumothorax (a collapsed lung that occurs when air enters the space around lungs); asthma (a condition in which the airways—the tubes that carry air in and out of the lungs—narrow and swell causing reversible obstruction); pleural effusion (an excessive collection of fluid in the pleural cavity); pulmonary edema (a condition where fluid accumulates in lung tissues); upper respiratory tract infections (such as a common cold); pneumonia (an infection of an air sac in one or more lungs such as bacterial or viral pneumonia); atypical pneumonia (an infection of the respiratory tract caused by pathogens that are not commonly associated with pneumonia); atelectasis (a condition where lungs collapse partially or completely); pulmonary fibrosis (a disease in which the lungs become scarred or fibrosed and damaged causing difficulty in breathing); and pneumonitis (inflammation of lung tissue not due to infection). Other respiratory tract diseases include those described by hypertext transfer protocol secure://en.wikipedia.org/wiki/Respiratory_disease (last accessed Oct. 23, 2019, incorporated by reference). Inhalable drugs that target the sites of these diseases in the respiratory system may be tested using the dissolution apparatus disclosed herein.

Such drugs include inhaled corticosteroids such as beclomethasone, budesonide, ciclesonide, flunisolide, fluticasone, or mometasone in a preparation designed to be inhaled through the mouth. Inhaled corticosteroids act directly in the lungs to inhibit the inflammatory process that causes asthma. Inhaled corticosteroids help to prevent asthma attacks and improve lung function. They may also be used in the treatment of certain other lung conditions, such as chronic obstructive pulmonary disease (COPD).

The apparatus and method disclosed herein may be used to test particles of pure drug free of excipients or particles of drug in admixture with an excipient such as a surfactant or pharmaceutical carrier.

In some embodiments, the apparatus and method may be used to evaluate dissolution of other kinds of inhaled drugs such as antibiotics, antimicrobial, antifungal, or antiparasitical medicines such as pentamidine, inhalable hormones such as insulin or human growth hormone, nicotine, cannaboids or other plant derived compounds. Such drugs include those which are locally administered and active in the respiratory system as well as those which are systemically administered via the respiratory system.

A next generation impactors (NGI) is an instrument that measures the reach range of a particulate substance as it moves through an opening with the use of aerosol An NGI has seven stages, five of which are in the range 0.5 to 5 microns plus a micro-orifice collector which acts as a final filter and a horizontal planar layout adopted for ease of operation and automation. The air flow passes through the impactor in a saw tooth pattern. Particle sizing is achieved by successively increasing the velocity of the air stream by forcing it through a series of nozzles containing progressively reducing jet diameters.

The resultant samples from each stage are collected in a series of collection cups. A removable tray holds all the sample collection cups such that all the cups can be removed and/or replaced in one single operation.

NGI are known in the art and are commercially available, for example, from Copley Scientific; hypertext transfer protocol secure://www.copleyscientific.com/home/inhaler-testing/aerodynamic-particle-size/next-generation-impactor-ngi (last accessed Oct. 22, 2019; incorporated by reference) or from MPS; hypertext transfer protocol secure://www.mspcorp.com/pharmaceutical/next-generation-impactor-ngi-170/(last accessed Oct. 22, 2019, incorporated by reference). Particle impactors are also described by and incorporated by reference to U.S. Pat. Nos. 6,453,758; 6,647,758 and 6,723,568.

Figure 2C:
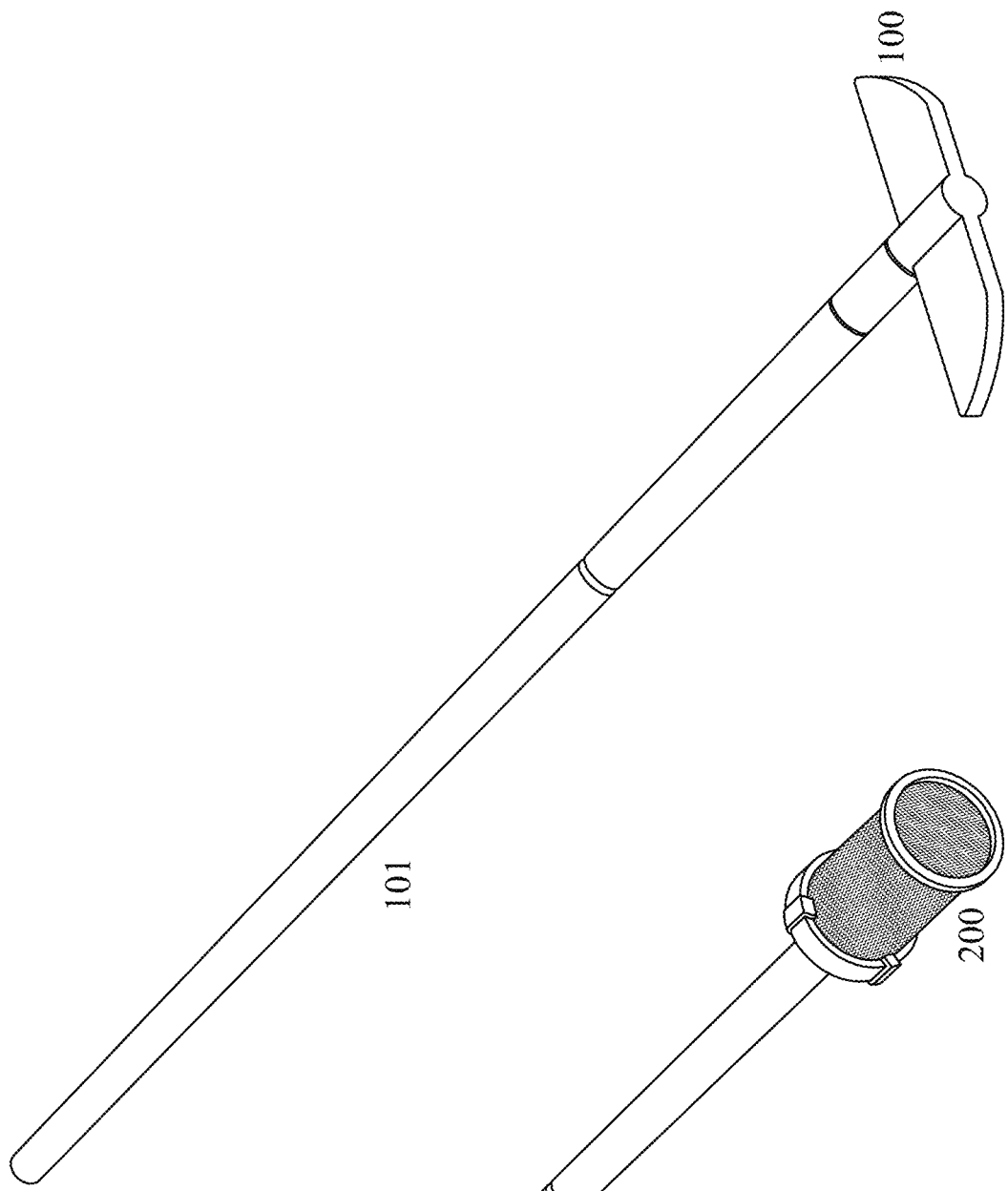
FIG. 2C depicts a paddle of a USP type 1 (paddle) drug dissolution system depicting paddle 100 and rotatable shaft 101. (USP pharmacopeia (2005) Chapter <601>).
Figure 2D:
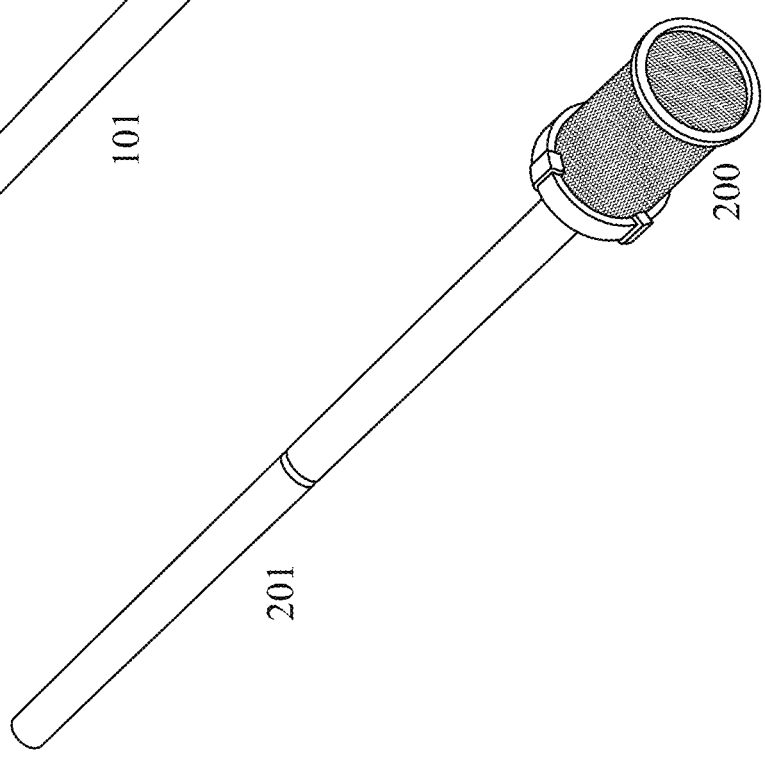
FIG. 2D depicts a basket of a USP type 2 (basket) dissolution system depicting basket 200 and rotatable shaft 201. USP pharmacopeia (2005) Chapter <601> (incorporated by reference).
Figure 2E:
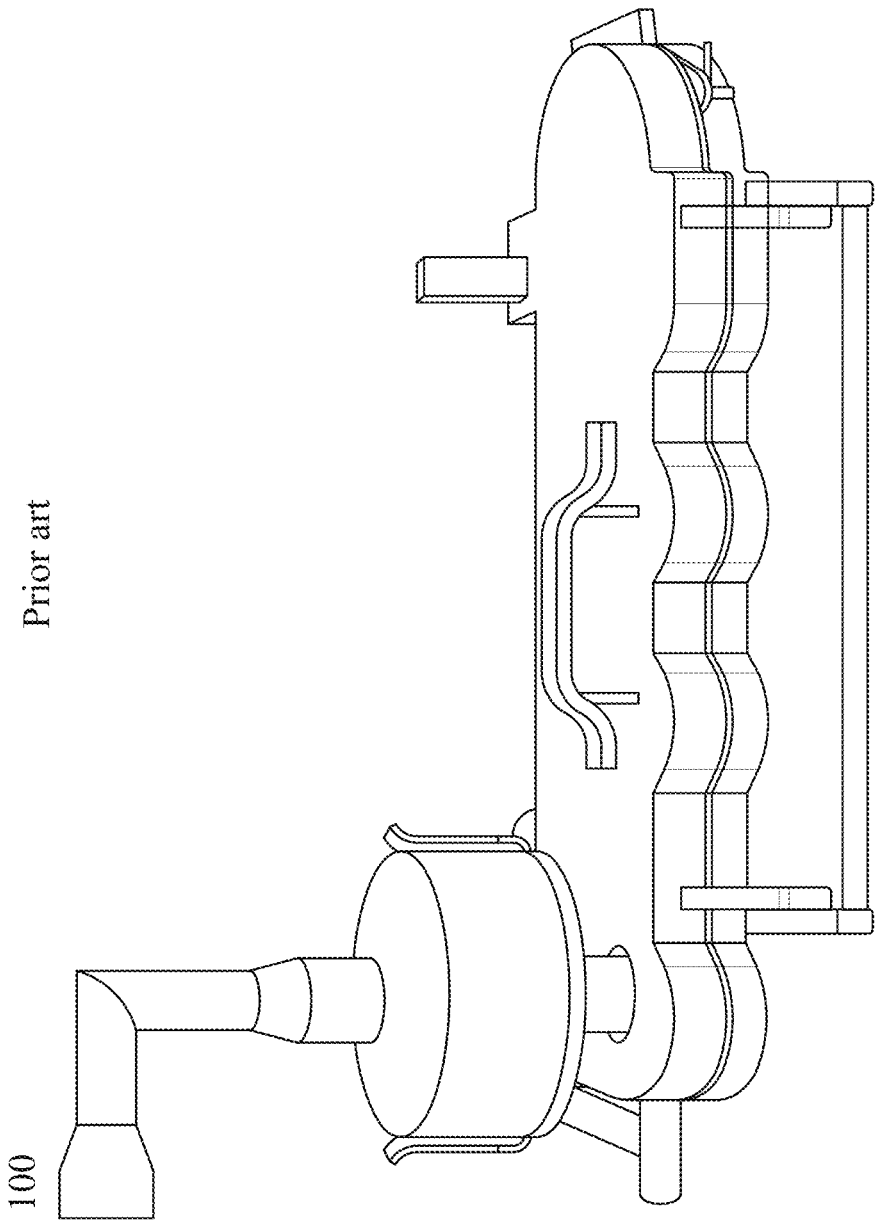
FIG. 2E shows a closed next generation impactor (NGI) where aerosol is fed into the opening 100 at the left top. Marple, et al., J Aerosol Med. 2003 Fall; 16(3):283-99; adapted from Copley, 2003, *Quality solution for inhaler testing*. Nottingham, UK.
Figure 2F:
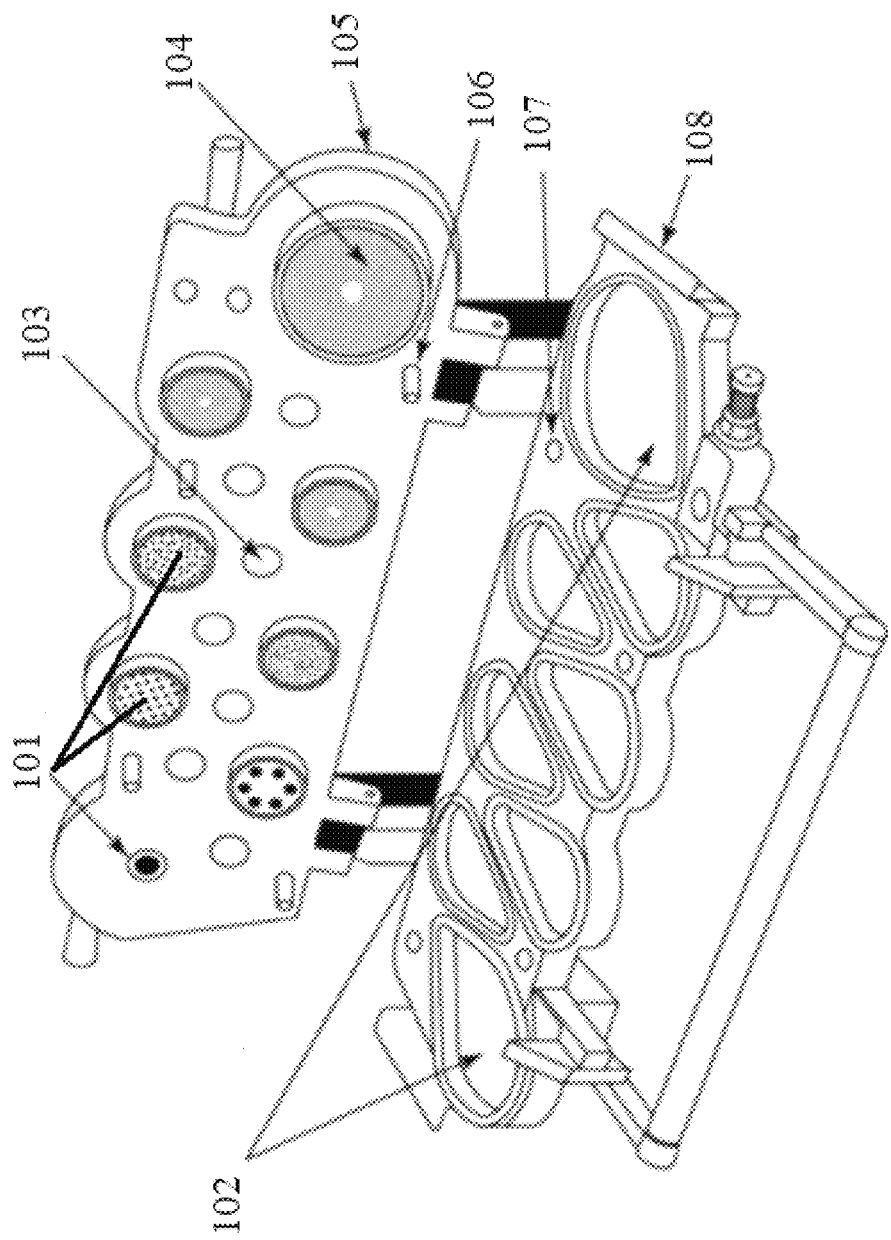
FIG. 2F shows an open next generation impactor (NGI). Removable cone-shaped cups 102 for receiving impacted drug particles of progressively decreasing sizes through interstage passageways 103 and then through the nozzles 101 shown at the top. Other elements include micro-orifice contactor 104, lid with seal 105, location pin 106, and bottom frame with cup tray in place 107. Marple, et al., J Aerosol Med. 2003 Fall; 16(3):283-99.); Adapted from Copley, 2003, *Quality solution for inhaler testing*. Nottingham, UK.

Examples of NGI are depicted by FIGS. 2E and 2F. NGI designs and design considerations are described by and incorporated by reference to Marple, V. A., et al., *Next Generation Pharmaceutical Impactor* (*A New Impactor for Pharmaceutical Inhaler Testing*): *Part* 1: *Design*, J. Aerosol. Med. 16(3) 283-299 (2003).

Figure 3A:
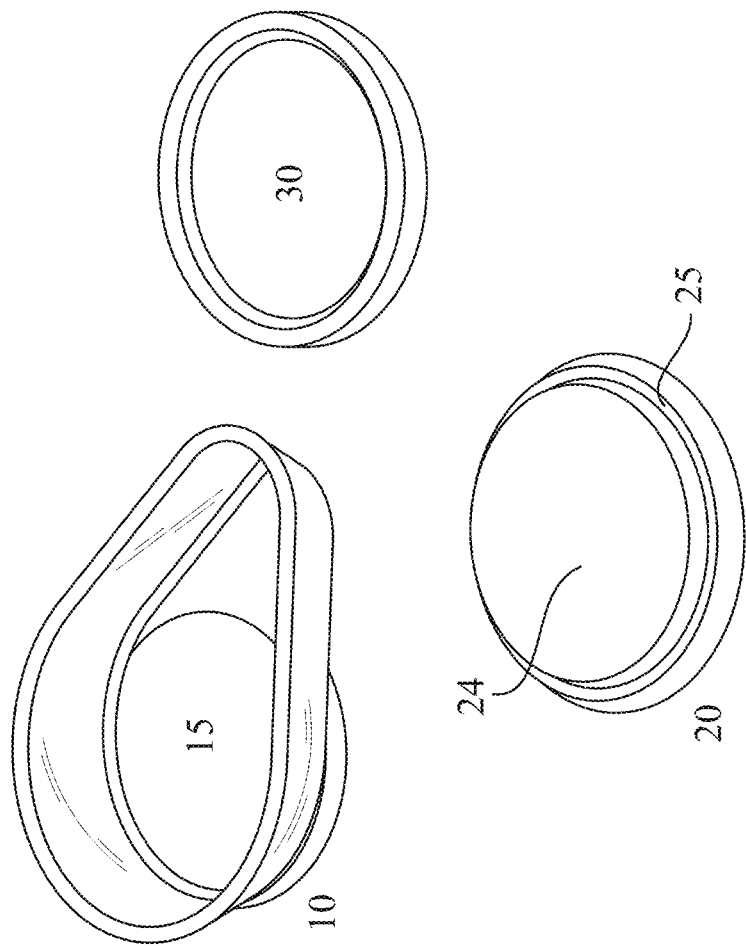
FIG. 3A illustrates parts of an NGI collection cup 10 modified to contain a hole 15 which fits an impaction insert 20; impaction insert 20 having a coin-shaped raised central portion 24 that fits through hole 15 and an annular peripheral flange 25; and a sealing ring 30 which can secure a lung simulation membrane over the central portion 24 of the impaction insert once removed from the collection cup.
Figure 3B:
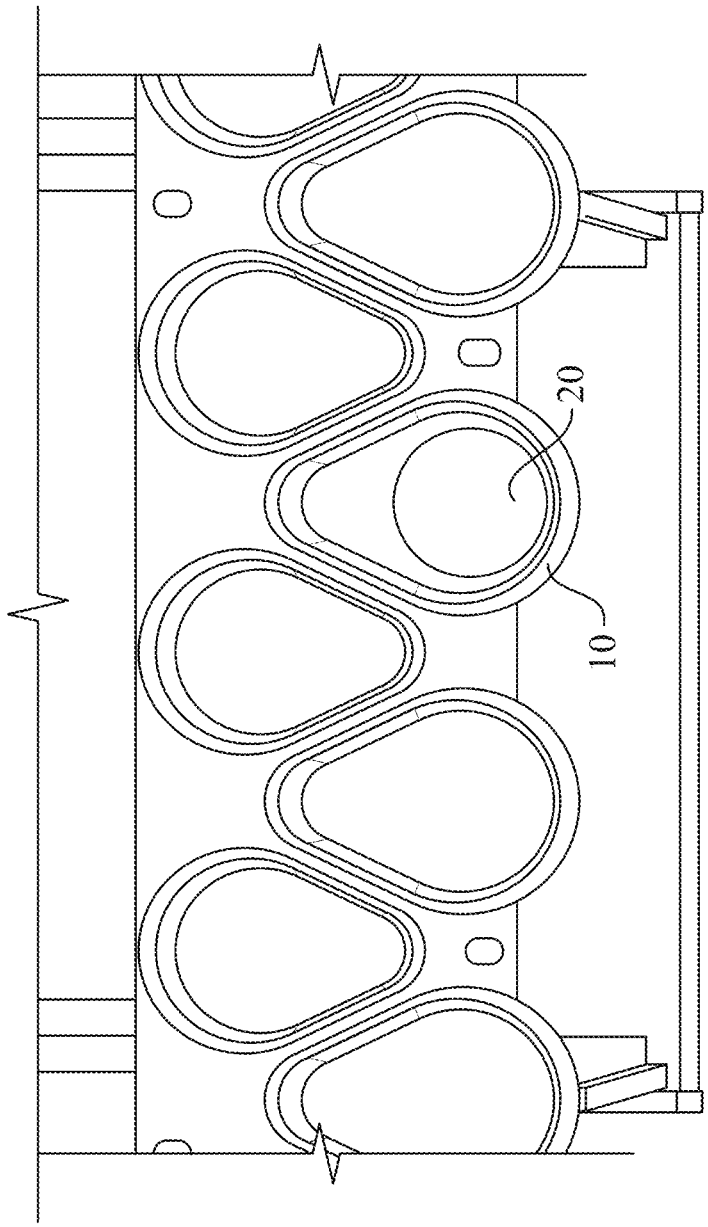
FIG. 3B depicts particle collection cups and a single modified particle collection cup 10 with an impaction insert 20. Marple, et al., J Aerosol Med. 2003 Fall; 16(3):283-99; Adapted from Copley, 2003, *Quality solution for inhaler testing*. Nottingham, UK.

In contrast to conventional designs, the inventors have modified the conventional cone-shaped collection cups of the conventional NGI (a) to contain a round hole fitting a circular impaction insert (b) and securing ring (c); see FIGS. 3A and 3B. Only one NGI collection cup, which collects drug particles of a particular size, may be modified as shown by FIG. 3B, or alternatively two, three, four, five, six, or seven (or all) collection cups may be modified to contain impaction inserts which collect drug particles of different sizes from the NGI.

Basket type or type 1 USP dissolution devices are known. Basket type dissolution devices contain a small basket into which a drug capsule or pill can be inserted and then submerged into a dissolution fluid; see FIGS. 2B and 2D. They differ from type II paddle-style dissolution devices in which a paddle is rotated to dissolve a drug in the dissolution fluid; see FIGS. 2A and 2C. USP type 2 dissolution devices are further described by Karande, et al., hypertext transfer protocol://dissolutiontech.com/DTresour/200602Articles/DT200602_A03.pdf (incorporated by reference).

In contrast to conventional basket-type USP dissolution devices, the modified apparatus as disclosed herein contains a basket that is sized and configured to contain a membrane-sealed collection cup impaction insert as depicted by FIGS. 3A and 3B. In some embodiments, the membrane sealed impaction insert is placed face up or face down into the basket through a movable or removable top. In other embodiments, it is placed face up or face down in the basket from the bottom of the basket which can be movable or removable. In some embodiments, the membrane sealed impaction disk is secured within the basket, for example, by fitting into a groove in the inside of the basket or with a clip or other fitting. Typically, following assembly of the impaction insert, membrane and securing ring, the assembly is transferred to the basket and a lid of the basket is closed.

The basket is submerged into dissolution medium contained in a vessel. The vessel may be a semihemispheric borosilicate glass vessel or other suitable plastic, glass or metal vessels. The vessel holds sufficient fluid to cover the membrane covered impact insert in the basket, for example, about 250, 500, 750, 1,000, 1,500, 2,000 ml of dissolution medium via a shaft, such as a stainless steel shaft. The basket may be described as a rotating basket which smoothly rotates at a speed suitable for dissolving a sample in the dissolution medium, for example from about 50, 100, 150 or 200 rpm, preferably about 100 rpm.

Different dissolution media may be used to assess dissolution properties of a drug for research or clinical purposes. The dissolution medium is selected based on the conditions present where the drug will be administered. For controlled batch-to batch quality control of a drug or for controlled comparisons of different preparations of drugs, such as a comparison between an existing approved drug and a new generic drug, a simple medium such as water, saline or phosphate buffered saline may be selected. To assess dissolution properties of a respiratory drug in particular patients or particular patient populations, a synthetic lung fluid modelling that of fluids in a specific type of patient may be selected.

Some non-limited examples of dissolution media include Survanta®: phospholipids 25 mg/mL (including 11.0-15.5 mg/mL disaturated phosphatidylcholine), triglycerides 0.5-1.75 mg/mL, free fatty acids 1.4-3.5 mg/mL, and protein content less than 1.0 mg/mL. Another example of a dissolution medium is an artificial lung fluid containing DPPC 4.8 mg/mL, DPPG 0.5 mg/mL, cholesterol 0.1 mg/mL, albumin 8.8 mg/mL, IgG 2.6 mg/mL, transferrin 1.5 mg/mL, ascorbate 140 µM, and urate 95 µM, glutathione 170 µM. One or more of the above ingredients or their chemical equivalents may be incorporated into a dissolution medium.

In some embodiments, the device disclosed herein may be used to evaluate dissolution properties of loaded of an active pharmaceutical ingredient (API) such as a drug administered to the respiratory system. In other embodiments, it may be used to evaluate quality of the drug that is drawn by a patient from the device.

In other embodiments, the dissolution fluid may be selected to determine one or more dissolution properties of a drug or other test material (e.g., solubility in distilled water, PBS, saline, mucous, respiratory fluids, etc.) or to model physiological conditions in the respiratory system of a patient (e.g., conditions found in different parts of the respiratory system, conditions during a respiratory disease or disorder asthma, or after exposure to prior drug or after exposure to smoke, chemical irritants, foreign particles, biological materials or irritants (e.g., histamine, serotonin, ECF, heparin), mucus, blood, leukocytes, red blood cells, pathogens, or cellular debris).

A dissolution medium may contain a buffer to maintain pH in a physiological range, such as from 6.5, 7.0 to 7.5. The dissolution medium may have a pH which is within the normal range of blood or lung pH, for example, from pH 7.35 to 7.45.

In some embodiments, a drug sample may be tested in a dissolution medium (or under an atmosphere) containing a concentration one or more atmospheric gases. For example, a dissolution medium may contain an amount of $CO_2$, $O_2$, $N_2$, or argon present in lung fluid during inhalation or exhalation. Thus, $CO_2$, $O_2$, $N_2$ or argon content may correspond to content of these gases in inhaled or exhaled air and their solubility in lung natural lung fluids. The atmospheric concentration of $CO_2$ is about 0.04%, that of oxygen about 21%, that of nitrogen about 78% and that of argon around 1%. However, in exhaled air the concentration of $CO_2$ rises to about 4% and oxygen can fall to about 16%.

Normal human body temperature ranges between 37.5 and 38.3 C. Body temperature may be higher up to about ≥38.5, 39, 40, 41 or 41.5° C. during a fever, hyperthermia or hyperpyrexia. Drug testing using the apparatus and methods disclosed herein may be at normal body temperature or at a depressed or elevated temperature, for example, a temperature likely to be found in the respiratory system or tissue to which a drug is administered. Accordingly, in some embodiments, the dissolution apparatus as disclosed herein may contain insulation to maintain a desired temperature or temperature sensors and temperature control devices, such as heaters or cooling elements, to maintain a desired or constant temperature during assessment of the dissolution properties of a drug.

The collection cup 10, impaction insert 15 and securing ring 20 may be made of any suitable material and are typically made of a metal such as stainless steel or aluminum.

EXAMPLES

Dissolution Test

Materials. Materials are purchased from Copley Scientific Limited. (Nottingham, UK). Erweka GmbH. (OttostraBe, Germany); Avanti Polare Lipid, Inc. (Alabaster, Ala., USA); and Sigma Aldrich Chemical Co. (St. Louis, Mo. USA).

Apparatus. The dissolution test is performed using a high-performance cascade next generation impactor, which classifies aerosol particles into size fractions. It tests metered-dose and dry-powder inhalers and other inhaled drug delivery devices such as nebulizers and nasal sprays. It can be used to test inhaled or nasally delivered drugs including those dispensed by metered-dose, dry powder, and aqueous droplet inhalers, nebulizers including jet, ultrasonic and vibrating mesh nebulizers; and nasal sprays including aqueous based, dry powder and propellant based sprays. The collection cups of the NGI were modified to hold a removable impaction insert as shown by FIGS. 3A and 3B. FIG. 3A depicts the modified collection cup 10, hole in collection cup 15, removable impaction insert 20 and securing ring 30.

Figure 4A:
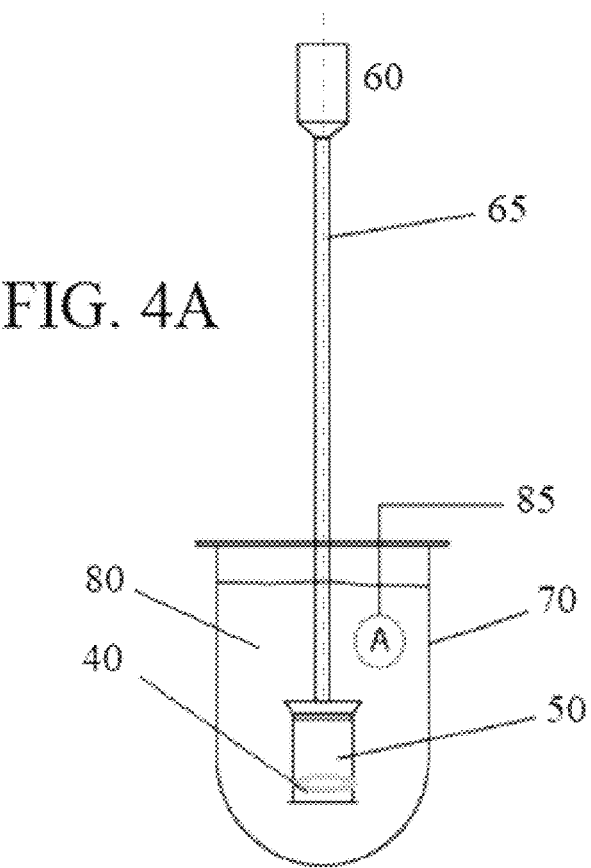
FIG. 4A depicts the various parts of the dissolution device of the invention including connection to motor or rotation device 60, rotatable shaft 65, basket 50, membrane-sealed impaction insert 40, vessel 70 and dissolution medium 80 and sampling point 85. USP pharmacopeia (2005) Chapter <601>.
Figure 4B:
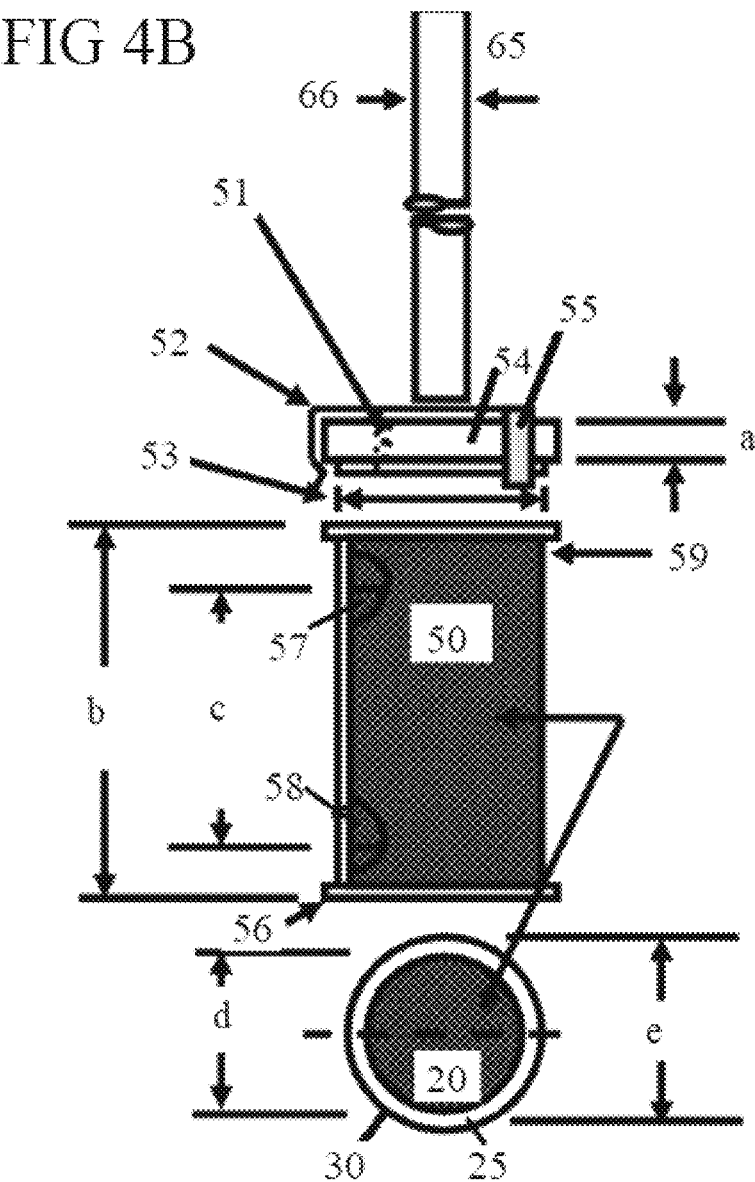
FIG. 4B depicts one embodiment of an assembly of the basket 50, impaction insert 20 and rotatable shaft 65 of the invention.

A modified USP Apparatus 1 dissolution tester type basket; Erweka DT141x/161x Tester station (Erweka GmbH. Germany) is employed to identify and characterize the dissolution properties of an active inhaled drug (fluticasone). A schematic diagram of modifications to the dissolution apparatus is shown in FIGS. 4A and 4B. Modifications include both an increased diameter of the basket (to accommodate the impaction insert) and an increased capacity of the dissolution vessel to accommodate the larger size of the basket. FIG. 4B describes the geometric size of modified basket.

In one embodiment as shown by FIG. 4B, the rotating shaft may be approximately 6.3 to 6.5 or 9.4 to 10.1 mm in diameter and be connected to a cap 54 and clasp 55 which may be approximately 5.1 in thickness (a). The cap may have a vent hole 51 about 2.0 mm (preferably 1-5 mm, 1.5-2.5 mm) in diameter and a retention spring 52 with three tangs on 120° centers. The top of the basket may have a clear opening 53 of 50-200 mm, preferably 75-150 mm or about 100.2 mm. In this embodiment, the basket has a cylindrical shell 25-50 mm preferably about 32 mm in height (b) and 10-50 mm preferably about 27.0 mm open screen (c). Elements 57 and 58 represent the open screen of the basket which in one embodiment is 10-50 mm preferably about 27.0 mm. The basket has bottom base 56. Membrane sealed impaction insert 20 has a central membrane-covered area (d) and a total diameter of 55-205 mm or about 105 mm (e), a peripheral annular portion 25 secured by ring 30. In other embodiments, the size of the device may be customized and thus the measurements described above may vary downward or upward by <5, 5, 10, 20, 30, 40, 50 or >50%. Those skilled in the art may select a mesh that permits circulation of dissolution fluid over or around the membrane covered impaction insert or disc while retaining the insert or disc in the basket.

Drug particle collection. The Next Generation Impactor (NGI) collects dispersed particles (e.g. corresponding to inhaled aerosol drug or dust) at a predetermined flow rate such as that described by Son et al. id. Flow rates include 30, 40, 50, 60, 70, 80 or 90 L/min.

The inhalation flow rate for dry powders depends on the type of inhalation device and inhalation volume of the patient. The inhalation flow rate for a metered dose inhaler ranges between about 28.0 and 28.8 L/min.

For the dissolution studies, the collection cup 10 is assembled together with the impaction insert 20 and secured with ring 30 into the NGI collection tray. Further description of the assembly involving the collection cup is incorporated by reference to Son, Y J, et al. *Development of a standardized dissolution test method for inhaled pharmaceutical formulations*. Int J Pharm 2009; 382(1-2):15-22.

Dispersed (inhaled) drug particles are actuated through the NGI at a required flow rate. As shown by FIG. 3B, the dispersed drug particles are collected in each unmodified collection cup and one modified collection cup 10 holding an impaction insert 20.

Figure 1C:
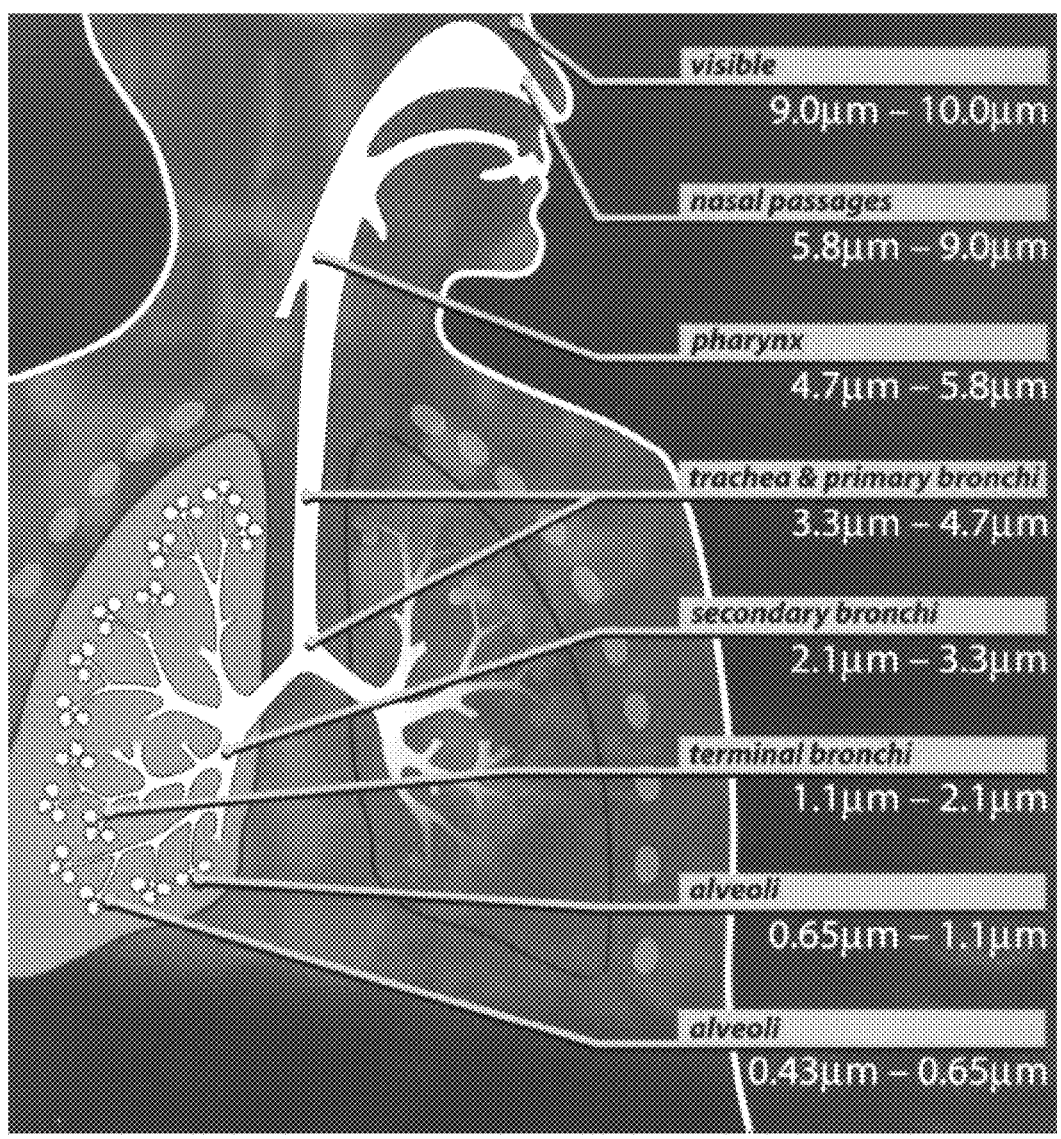
FIG. 1C describes approximate sizes of particles impacting different parts of the respiratory system. Adapted from Copley, 2003, *Quality solution for inhaler testing*. Nottingham, UK.

Particle size dictates where aerosolized particles deposit in the respiratory tract. For drugs intended to target trachea and primary bronchi a particle size of 3.3 to 4.7 µm may be selected; for drugs that target secondary and terminal bronchi a particle size of 1.1 to 3.3 µm may be selected and for drugs intended to target alveoli in the lungs a particle size of 0.45 to 1.1 µm may be selected for dissolution testing. Other selectable particle size ranges and the corresponding tissues impacted are shown by FIG. 1C.

Membrane. Any membrane that is porous and sufficiently flexible for use in the dissolution device as described herein may be used, preferably, the membrane is a polycarbonate membrane (PC) or with polyvinylidene difluoride membrane (PVDF). Both hydrophilic and hydrophobic membranes may be selected depending on the chemical properties of the drug being tested.

Some embodiments may employ a porous membrane that is a polyethersulfone membrane, a polysulfone membrane, a glass fiber, a nylon membrane, a polyester membrane, a polycarbonate membrane, a polypropylene membrane, a polyvinylidene difluoride membrane, a cellulose membrane, a nitrocellulose membrane, a cellulose acetate membrane, a nitrocellulose mixed ester membrane, a polyurethane membrane, a polyphenylene oxide membrane, a poly(tetrafluoroethylene-co-hexafluoropropylene membrane, a cellulose phosphate membrane, a cellulose/silica gel paper, a borosilicate glass membrane, a quartz membrane, or a combination thereof.

The membrane will have a pores size sufficient to permit dissolved drug to move into the dissolution buffer, for example, a pore size ranging from 0.1, 0.2, 0.5, 1, 2, to 5 μm, preferably about 0.22 or 0.45 μm. In some embodiments membrane thickness ranges from 50, 75, 100, 125 to 150 μm. In a preferred embodiment, the porosity of the membrane ranges from about 2, 3, 4 to 5 μm.

Sealing of drug particles impacted on impaction insert. Following impaction of inhaled drug, the impaction insert is removed, the side containing impacted drug particles is covered with a membrane and the membrane is sealed in placed using a ring which fits over a peripheral annular surface of the impaction insert. Further description of the impaction method is given by, and incorporated by reference to, the NGI manual and pharmacopeia (Marple, et al., J Aerosol Med. 2003 Fall; 16(3):283-99) or by Son, Y J, et al. *Development of a standardized dissolution test method for inhaled pharmaceutical formulations*. Int J Pharm 2009; 382(1-2):15-22 who described a method of using membrane-modified collection cups.

After sealing the impaction insert is placed into the basket and separately soaked in a dissolution media contained in a vessel into which the basket is submerged. This process is repeated with several different dissolution media including simulated lung fluid (SLF), 0.2 M phosphate buffer (pH 7.4), phosphate buffered saline (PBS), modified PBS (mPBS) containing dipalmitoylphosphatidylcholine (DPPC), and PBS containing polysorbate 80 (tPBS). The basket is then rotated by the shaft at a speed of 100 rpm.

In one embodiment the following steps are performed:

The NGI device is assembled.

The dispersion (inhalation) device is loaded with a dosage of fluticasone or other drug to be tested and attached to the NGI induction port which receives the dispersed drug.

The flow rate of the NGI is adjusted, for example, to a rate of about 60 L/min for fluticasone and the flow is activated thus impacting drug particles on the surfaces of the collection plates in the modified NGI.

The flow is terminated and the NGI device is disassembled to retrieve one or more impaction inserts (collection plates) of the modified device.

These inserts, which contain impacted drug particles, are covered by a lung simulation membrane.

The impaction insert and membrane are locked together using a securing ring and transferred into the modified dissolution basket which is then attached to the rotatable basket shaft.

The basket containing the sealed impaction insert is inserted into the vessel part of the dissolution apparatus and a dissolution medium, such as simulated lung fluid, is filled into the vessel so as to cover the impaction insert. Alternatively, the basket is immersed in dissolution medium already in the vessel.

The dissolution apparatus is activated and the basket is rotated at a speed of 100 rpm for 5 minutes.

1 ml samples of dissolution fluid are removed every minute and replaced with a fresh equivalent volume of dissolution medium.

The concentration of fluticasone in these samples is determined by chromatographic analysis using an HPLC system with UV detection.

Data generated are expressed as the mean±SD. The statistical differences of release rates were studied by calculating a similarity factor, $f_2$. Statistical analytic methods are incorporated by reference to Martin R J, et al., Systemic *effect comparisons of six inhaled corticosteroid preparations*. Am J Respir Crit Care Med 2002; 165(10):1377-1383, incorporated herein by reference in its entirety. For curves to be considered similar, $f_2$ values should be close to 100. Generally, $f_2$ values greater than 50 (i.e., 50-100) ensure sameness or equivalent of the two curves.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A dissolution device, comprising:
a rotatable shaft,
a cylindrical basket,
an impaction insert from a particle impactor, and
a vessel,
wherein the basket is attached at its top to the rotatable shaft,
wherein the basket contains the impaction insert, and
wherein the shaft holds the basket within the vessel so that it is immersed when the vessel is filled with a dissolution medium.

2. The dissolution apparatus of claim 1, wherein the basket is configured to hold an impaction insert from a collection cup of a next generation impactor (NGI).

3. The dissolution apparatus of claim 1, wherein the impaction insert is round and has a diameter equal to the inside diameter of the cylindrical basket so as to fit within the cylindrical basket.

4. The dissolution apparatus of claim 1, wherein a bottom base and a top base of the basket are about 90.2 to 110.2 mm in diameter.

5. The dissolution apparatus of claim 1 wherein the basket has a height of about 33 to 41 mm.

6. The dissolution apparatus of claim 1, wherein the basket comprises a clip or fitting for attaching its top base to the rotatable shaft.

7. The dissolution apparatus of claim 1, wherein the basket comprises a fitting for attaching its top base to the rotatable shaft and wherein the fitting comprises a retention spring and a vent hole.

8. The dissolution apparatus of claim 1, wherein the basket comprises cylindrical open mesh shell comprises stainless steel, aluminum or other metal.

9. The dissolution apparatus of claim 1, wherein the cylindrical open mesh shell of the basket ranges from #20 to #40 mesh.

10. The dissolution apparatus of claim 1, wherein the cylindrical open mesh shell of the basket has mesh openings ranging from 0.1 mm to 1.0 mm in diameter.

11. A system comprising:
a next generation impactor (NGI) comprising a collection cup having a removable impaction insert in one or more of its collection cups, and the dissolution device of claim 1.

12. The system of claim 11, further comprising a drug impacted on the impaction insert.

13. The system of claim 11, further comprising an inhalable anti-inflammatory drug impacted on the impaction insert.

14. The system of claim 11, wherein the lung simulation membrane is a polycarbonate membrane or is a polyvinylidene difluoride (PVDF) membrane.

15. The system of claim 11, further comprising a rotary mixture attached to the rotatable shaft and/or a chromatography system suitable for determining the concentration of a drug in the aqueous medium.

16. A method for determining dissolution properties of an aerosolized drug comprising applying the drug to a next generation impactor (NGI) under conditions suitable for impacting particles of the drug in collection plates of the NGI, recovering impacted drug particles on one or more impaction inserts from the collection plates, sealing the one or more collection plates in a lung simulation membrane, inserting the collection plate sealed within the lung simulation membrane into the cylindrical basket of claim 1, submerging the cylindrical basket containing the lung simulation membrane covered impaction inserts in a dissolution medium contained in a vessel, and detecting an amount of the drug which dissolves into the dissolution medium.

17. The method of claim 16, wherein the dissolution medium is water, phosphate buffered saline, or a simulated lung fluid.

18. The method of claim 16, wherein the impaction insert contains drug particles ranging in size from 0.45 to 1.1 μm in diameter.

19. The method of claim 16, wherein the impaction insert is sealed with a polycarbonate or polyvinylidene difluoride (PVDF) membrane.

20. The method of claim 16, wherein the amount of drug dissolved into the dissolution medium is detected after a period of no more than 15 minutes.

* * * * *